United States Patent [19]

Casebeer et al.

[11] Patent Number: 5,423,840

[45] Date of Patent: * Jun. 13, 1995

[54] KERATOREFRACTIVE DIAMOND BLADE AND SURGICAL METHOD

[75] Inventors: J. Charles Casebeer, Flagstaff, Ariz.; Carol A. Rae, Rapid City, S. Dak.

[73] Assignee: Chiron Vision Corporation, Irvine, Calif.

[ * ] Notice: The portion of the term of this patent subsequent to Jun. 29, 2010 has been disclaimed.

[21] Appl. No.: 83,994

[22] Filed: Jun. 28, 1993

Related U.S. Application Data

[63] Continuation of Ser. No. 865,300, Apr. 8, 1992, Pat. No. 5,222,967.

[51] Int. Cl.⁶ ............................................. A61B 17/32
[52] U.S. Cl. .................................. 606/166; 128/898; 606/167
[58] Field of Search ............... 606/107, 166, 167, 181; 128/898; 30/346.54, 350, 357

[56] References Cited

U.S. PATENT DOCUMENTS

| | | |
|---|---|---|
| 2,049,898 | 8/1936 | Driest . |
| 2,102,930 | 12/1937 | Wharton . |
| 2,649,860 | 8/1953 | Royer . |
| 3,610,246 | 10/1971 | Salmon ........................... 606/167 |
| 3,945,117 | 3/1976 | Beaver . |
| 4,185,634 | 1/1980 | Freedman . |
| 4,602,630 | 7/1986 | Anis . |
| 4,674,503 | 6/1987 | Peyman et al. . |
| 5,071,427 | 12/1991 | Stahl . |
| 5,201,747 | 4/1993 | Mastel . |

FOREIGN PATENT DOCUMENTS

| | | |
|---|---|---|
| 0139169 | 5/1985 | European Pat. Off. . |
| 0261242 | 3/1988 | European Pat. Off. . |
| 3118673 | 11/1982 | Germany . |
| 1424814A | 9/1988 | U.S.S.R. . |

OTHER PUBLICATIONS

Herbert, Stan, "The Diamond Knife Rather More Than Meets the Eye," *Industrial Diamond review* May, 1984.
Codman/Micra, "Titanium Instruments and Diamond Knives for Opthalmology," Jan. 1985, Printed in USA, Dist. by Codman Randolph Mass. pp. 1–6.
Waring, "Repeated Surgery for Residual Myopia and Hyperopia After Refractive Corneal Surgery" In: Waring G. O. ed. "Refractive Keratotomy for Myopia and Astigmatism," St. Louis Mo.; Musby Yearbook Inc., 1991 pp. 641–668.
Bores, "Historical Reiew and Clinical Results of Radial Keratotomy in Binder P. S. ed." International Ophthalmology Clinics Refractive Corneal Surgery: The Correction of Aphahia, Hyperopia and Myopia, Boston, Mass.: Little, Brown and Co., 1983; 23: 93–118.

*Primary Examiner*—Peter A. Aschenbrenner
*Attorney, Agent, or Firm*—Pravel, Hewitt, Kimball & Krieger

[57] ABSTRACT

A keratorefractive surgical blade has opposing sides and first and second edges which intersect each other to form a point. The first edge is shaped to form a sharp cutting edge extending from the point a predetermined distance shorter than the distance from the base of a surgical incision to Bowman's membrane, a portion of the first edge adjacent to the sharp cutting edge being dull relative to the cutting edge.

A method of performing keratorefractive surgery, includes the steps of:
 (a) plunging a cutting edge of a surgical blade into the cornea of a human eye at a point between the edge of the optical zone and the limbus at a controlled depth;
 (b) cutting an incision at said controlled depth along a relatively straight line between the optical zone and limbus;
 (c) shaping the profile of the incision by moving a cutting edge of a blade which is shorter than the distance from the base of the incision to Bowman's membrane, along the incision at substantially the same controlled depth of step (b); and
 (d) withdrawing the blade from the incision.

5 Claims, 4 Drawing Sheets

KERATOREFRACTIVE DIAMOND BLADE AND SURGICAL METHOD

This is a continuation of application Ser. No. 865,300 filed Apr. 8, 1992 now U.S. Pat. No. 5,222,967.

BACKGROUND OF THE INVENTION

The present invention relates to diamond blades for use in eye surgery and a novel method for performing a radial keratotomy/keratorefractive (RK) surgical procedure. More particularly, the invention is directed to a novel blade design and method which allow corneal incisions in an RK procedure to be made more effectively and efficiently.

Radial keratotomy RK is a surgical procedure intended to correct myopia (near sightedness). During the procedure, the surgeon uses a diamond-bladed knife to make 4 or more spoke-like radial cuts of a controlled depth in the paracentral and peripheral cornea to produce a flattening effect on the cornea. Exact incisions and a precise depth of cut are important so that the correction of curvature of the cornea is not too great or not great enough.

The knife blade is held by a handle which normally includes a pair of footplates positioned on either side of the blade, which are designed to slide along the outer surface of the cornea. The location of the footplates relative to the tip of the blade can be adjusted by a micrometer setting to control the depth of cut.

Since an RK procedure involves cutting the cornea of a human eye, great care must be taken to make sure that the cuts are precise and at the depth necessary to provide for the indicated correction. Consistent results are difficult to achieve. A problem which has been known to occur is an under correction of the myopia through cuts which are not as deep or precise as indicated. Cuts are normally made conservatively because the knife is extremely sharp and many surgeons tend to be over-cautious when the knife is close to the optical zone.

Several RK surgical procedures are popular in the United States. One is known as the American method, where an initial wound is formed by plunging the knife at the edge of the optical zone marked on the cornea, and moving the knife away from the optical zone. Another method, known as the Russian method, involves making the initial wound at the limbus or outer portion of the cornea and cutting toward the optical zone, ending at the edge of the optical zone marked on the cornea.

Even though the American style is considered to be more comfortable to use since the knife is plunged initially at the edge of the optical zone so the possibility of impinging on the optical zone at the end of the cut is minimized, the cut is not squared off at the optical zone because of the normal travel path of the knife during initial plunge. Also, because of vector forces acting on the knife, a uniform cut at the proper depth is difficult to make along the entire incision without excessive pressure being exerted, through the footplates of the knife on the outer surface of the cornea.

While the Russian method tends to result in cuts that are more squared off toward the edge of the optical zone and requires less cutting pressure, many surgeons tend to be more tentative at the end of the cut in order to avoid impinging on the optical zone. This tends to result in an incision which does not extend up to the edge of the optical zone.

Another problem that occasionally arises is that the knife blade is not properly set during an incision. It is difficult to retrace the cut at the proper setting without straying from the exact path of the initial cut.

It would be advantageous to the surgeon to combine the safety of the American style with the efficiency and more predictable results of the Russian style by the squaring off of incisions at the edge of the optical zone. It would also be advantageous to provide a surgical knife which can be used to square off incisions after an initial cut is made without having to worry about cutting new tissue outside of the initial incision.

SUMMARY OF THE INVENTION

The invention is directed to a novel blade for a surgical knife, which is useful in forming incisions in RK surgery, and to a novel method for forming such incisions more effectively and accurately. The keratorefractive blade can be designed to fit into a holder of a type presently used, which grabs the shank of the blade and holds it in place during surgery. A micrometer adjustment controls the depth of cut by adjusting the distance the tip of the blade extends beyond the footplates.

The blade has opposing, flat sides defined by at least two edges which intersect each other at an acute angle to form a point or tip. A typical blade has what is called a reverse edge which can be parallel to the axis of the knife and a forward edge which is formed at an angle relative to the reverse edge. One of the edges, preferably the reverse edge, has a portion shaped to form a short, sharp cutting edge or enhancement portion, which extends from the tip to a portion of the reverse edge which is relatively dull and will not cut tissue.

The length of the enhancement portion is shorter than the distance between the base of the incision and the corneal layer known as Bowman's membrane, which is located just under the epithelium and above the corneal stroma. For example, the enhancement portion should be 0.05–0.40 mm, as compared to a typical RK incision which is 0.50–0.75 mm deep. The enhancement edge is preferably formed at a small angle relative to the remaining portion of the edge of the blade on which it is formed, for example, from 5°–10°. This angle allows the enhancement cutting edge to be formed between a pair of beveled surfaces formed along planes parallel to the enhancement edge, so that the remaining portion of the reverse edge is relatively dull.

In one preferred embodiment, the blade could be a typical flat knife blade with a forward edge formed at a preferable angle of about 35°–45° relative to the reverse edge. The short enhancement portion, which extends from the tip, is formed by beveling adjacent sides of the reverse edge of the blade at about 45° without sharpening the forward edge or adjacent portion of the reverse edge.

This embodiment can be used at the time of the initial surgery or post-operatively to enhance an incision made by either surgical method described above. For example, for an incision already made by a conventional blade using the American method (cutting from the optical zone to the limbus), and using the enhancement part of the blade to retrace the initial cut in the opposite direction, an incision results which is smooth and flat with a square end at the optical zone. This procedure allows the surgeon to combine the comfortable feel of the American style with the squared off cut at the optical zone of the Russian style. This embodiment could also be used to enhance an incision formed by the method (cutting from the limbus to the optical zone) if the initial depth setting was wrong or a post-operative exam reveals the incision was not close enough or deep enough at the optical zone.

In an alternative preferred embodiment, in addition to an enhancement portion formed on the reverse edge of the blade, the forward edge is also sharpened to make the blade universal in the sense the same blade can also be used to form the initial incision when the American style is used. This second embodiment allows the initial cut to be made by moving the forward edge of the blade from the optical zone toward the limbus, and the forming and shaping to be performed by the reverse edge when the blade is drawn back along the incision toward the optical zone. The enhancement portion of this blade could also be used for the other purposes described above for the first embodiment.

BRIEF DESCRIPTION OF THE DRAWINGS

A better understanding of the invention can be obtained when the detailed description of exemplary embodiments set forth below is reviewed in conjunction with the accompanying drawings, in which.

DETAILED DESCRIPTION OF EXEMPLARY EMBODIMENTS

Figure 1:
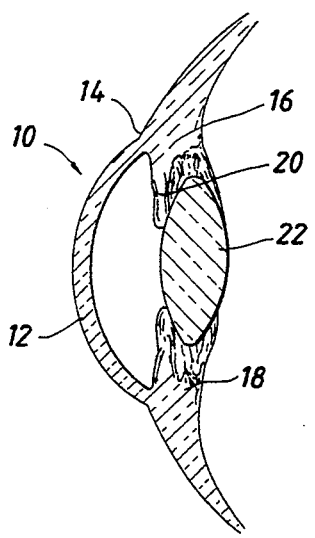
FIG. 1 is a schematic view in cross section of a typical human eye showing, in particular, the cornea and other elements defining the anterior chamber.
Figure 2:
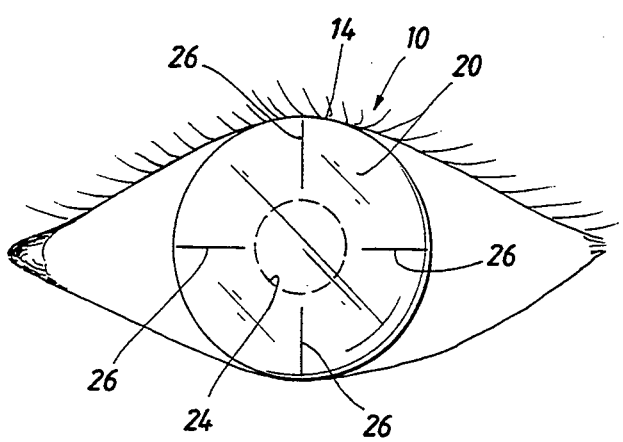
FIG. 2 is a front, schematic view of the human eye showing, for example, typical incisions made through a radial keratotomy surgical procedure.

Before describing the invention in detail, reference should be made to FIG. 1 which shows the anatomy of a human eye generally designated by reference numeral 10. The outer surface of the eye 10 is formed by a cornea 12 which terminates at the corneal margin or limbus 14 in the vicinity of an anatomical protuberance on the inner surface of the cornea known as a scleral spur 16. A ciliary muscle 18 joins an iris 20 and is connected to a lens 22 which is caused by the ciliary muscle to flex in order to focus the vision of the subject. Referring to FIG. 2, the iris 20 defines an optical zone, illustrated by dotted lines 24 within which light passes through the lens 22 onto a retina (not shown) for transmission of an image to the optical nerve and brain.

When a patient is myopic or near sighted, the cornea tends to have a greater curvature than necessary, which causes the focal point of images entering the eye to be offset from the retina. It has been found that myopia can be surgically corrected by forming a number of incisions such as those designated by reference numeral 26 of FIG. 2 in the outer surface of the cornea 12, which have the effect of flattening the cornea. These incisions preferably extend from the edge of the optical zone 24 to within 0.5 millimeter of the limbus 14.

Various methods have been described above for forming the incisions 26. These methods include the American method where the knife is plunged initially at the edge of the optical zone (which is marked by the surgeon with dotted lines similar to those designated by reference numeral 24 in FIG. 2) and moved toward the limbus 14, and the Russian method where the incision is formed by moving the knife from the limbus toward the optical zone.

Figure 3:
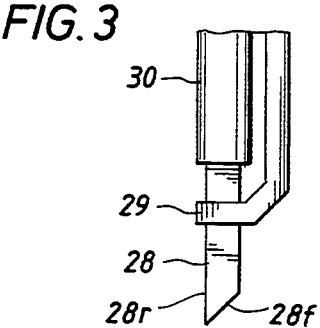
FIG. 3 is a partial side plan view of a typical keratorefractive knife.
Figure 4:
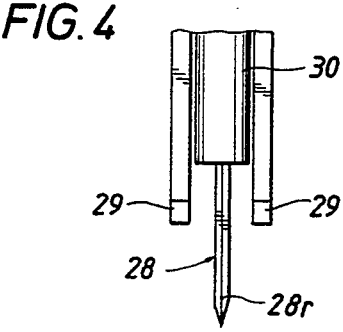
FIG. 4 is a partial front plan view of the knife of FIG. 3.

One aspect of the present invention is a novel diamond bladed knife which allows keratorefractive surgery to be performed by using either method, where corrections or enhancements to an initial cut can easily be made. The subject knife is an improvement on a diamond bladed knife blade typically used in RK procedures, shown generally in FIGS. 3 and 4, where a blade 28 formed of industrial diamond is mounted in a hand piece 30. The blade 28 is normally sharpened on both a forward edge 28f and a reverse edge 28r. A pair of footplates 29 straddle the blade 28 and are designed to slide along the outer surface of the cornea 12 during the surgical procedure for controlling the depth of cut, with the distance the tip of the blade 28 projects beyond the footplates 29 being controlled by a micrometer setting of known design (not shown).

Figure 5:
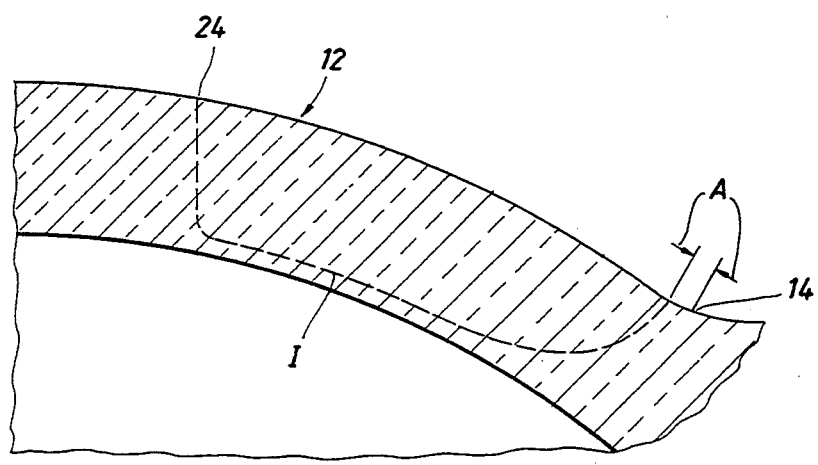
FIG. 5 is a schematic view of a section of a cornea showing the outline of a proper RK incision.

An ideal RK incision formed by such a knife is shown in FIG. 5 where the dotted lines I illustrate a profile of the cut. The incision I should have a depth of about 95% of the depth at the site pachymeter, typically 0.50-0.75 mm. The edge of the incision I at the optical zone 24 should be formed perpendicular to the outer surface and squared off in order to provide the indicated flattening necessary to alleviate the patient's myopia. The bottom of the incision should be smooth and extend toward the limbus 14 where the incision gradually terminates at about 0.5 mm from the limbus as illustrated by arrows A.

Figure 6:
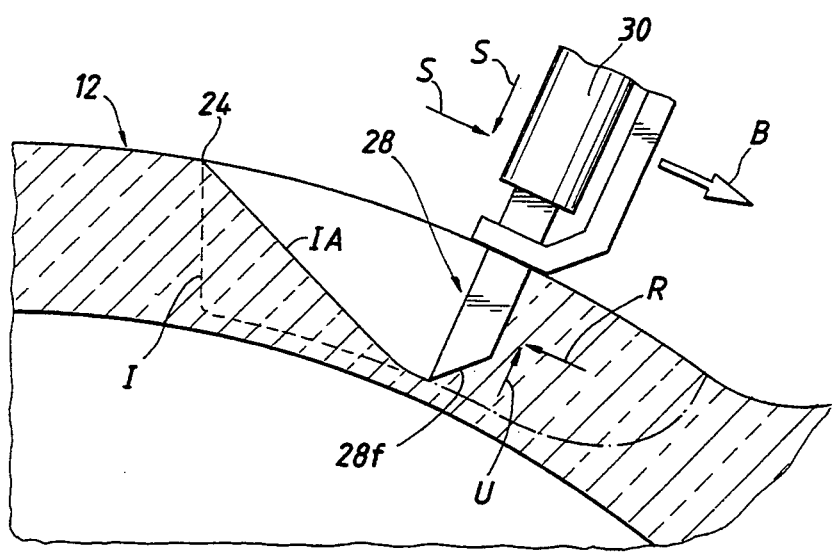
FIG. 6 is a schematic view showing an RK incision made in accordance with the American method.

This type of incision I is difficult to achieve when the American method is used, as shown in FIG. 6, where a typical incision IA formed by the American method is illustrated in exaggerated fashion. In such a procedure the knife blade 28 is initially plunged into the cornea 12 at the optical zone 24. The forward edge 28f does the cutting as the knife 30 is moved away from the optical zone 24 in the direction of arrow B.

Instead of forming a squared off cut at the optical zone 24, as illustrated by the dotted lines I, the knife blade 28 might typically form an incision with a profile IA. This is because the corneal tissue exerts an upward resistive force against the angled forward edge 28f, shown by arrow U, in addition to the resistance to forward movement shown by arrow R. These forces require the surgeon to push downwardly as well as in the direction of the cut, shown by arrows S, S, which could result in an uneven depth of cut or excessive downward pressure exerted on the outer surface of the cornea.

Figure 7:
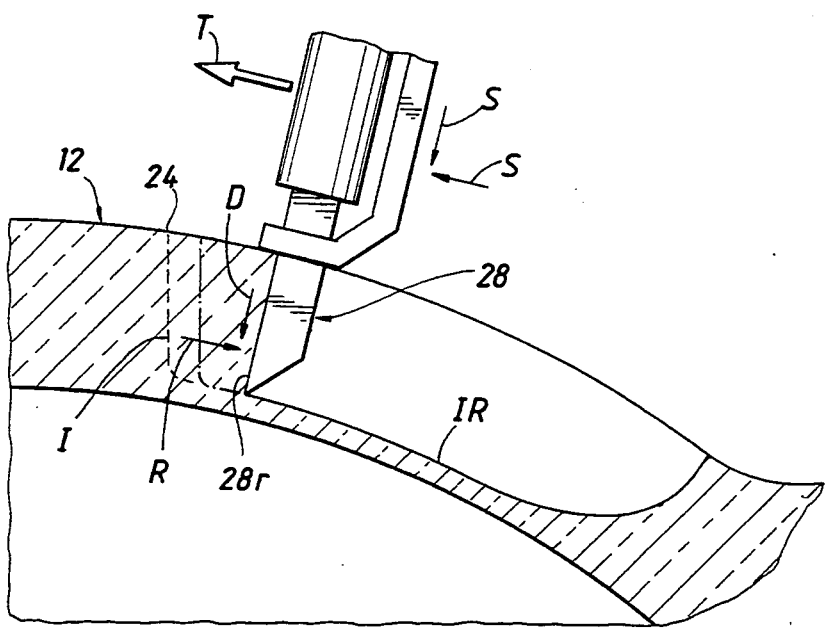
FIG. 7 is a schematic view showing an RK incision made with the Russian method.
Figure 8:
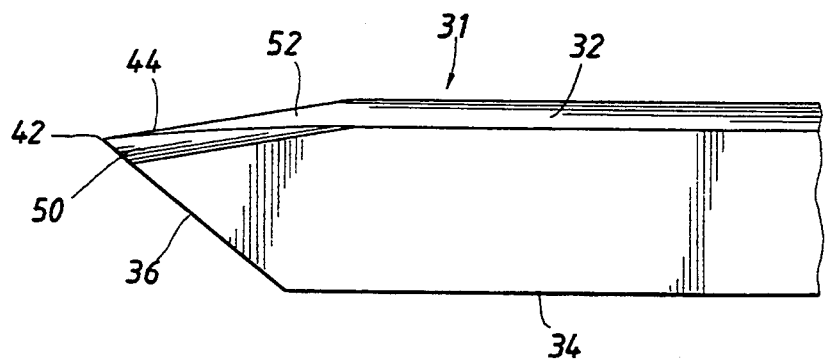
FIG. 8 is a perspective view of the cutting portion of the embodiment of the blade of the present invention.

When the Russian method is used, shown in FIG. 7, the reverse edge 28r does the cutting. The knife 30 is initially plunged near the limbus 14 and is moved toward the optical range 24 in the direction of arrow T to form an incision which could have a profile IR. Since the reverse edge 28r is not angled, resistive forces acting on the blade 28 are downward and against the direction of movement as shown by arrows D, R, respectively. These forces tend to push the blade downwardly as the surgeon moves the blade by exerting force in the direction of arrows S. However, since the resistive forces exerted by the corneal tissue tend to push the blade into the incision, less downward force is required and a more even cut is obtained than for the American method.

Since the incision IR is cut toward the optical zone 24, there can be a tendency for the surgeon to slow down or remove the blade before it reaches the edge of the optical zone, resulting in an incision which might have a profile IR, shown in FIG. 7, where the cut is not squared off or formed up to the edge of the optical zone 24. This could result in the need for post-operative enhancement if the cornea is not flattened sufficiently.

The knife blade which forms one aspect of the present invention can be used to make desired corrections to an incision with either profile IA or IR. The blade has what is called an enhancement portion since it can be used to enhance the initial cut without expanding the incision significantly. This is accomplished through the use of a very short cutting edge or enhancement portion formed on the reverse edge of a blade that is described in detail below.

Figure 10:
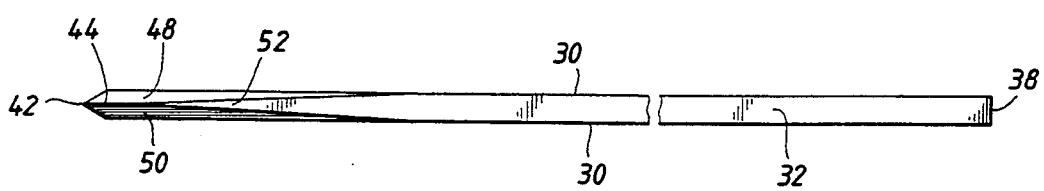
FIG. 10 is a top plan view of the blade of FIG. 8.
Figure 9:
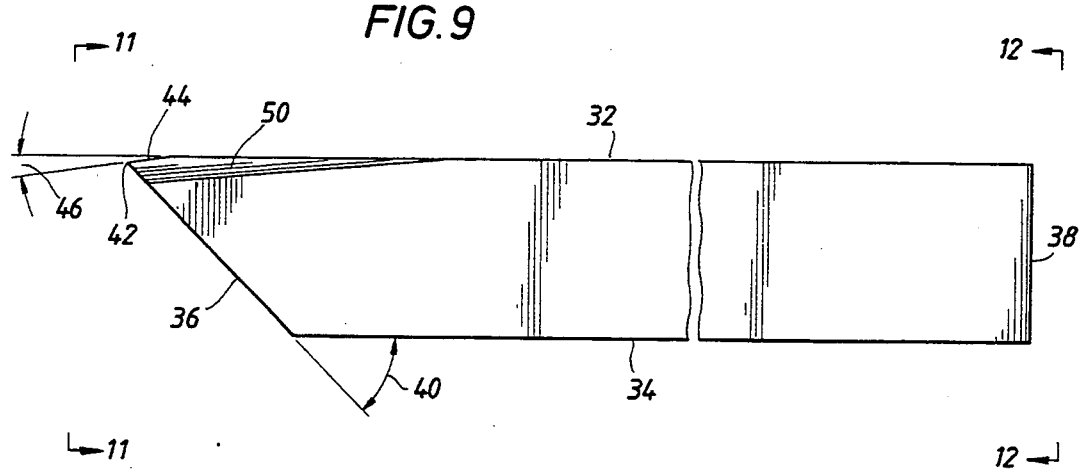
FIG. 9 is a side plan view of the blade of FIG. 8.
Figure 11:
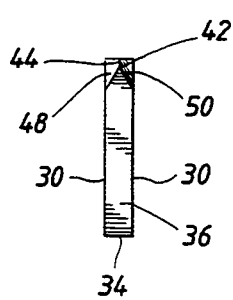
FIG. 11 is a front end view looking along the site line 11—11 of FIG. 10.
Figure 12:
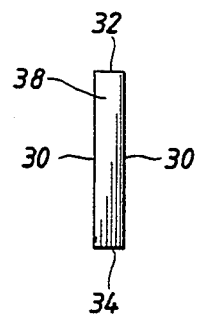
FIG. 12 is a rear end view looking along the site line 12—12 of FIG. 9.
Figure 14:
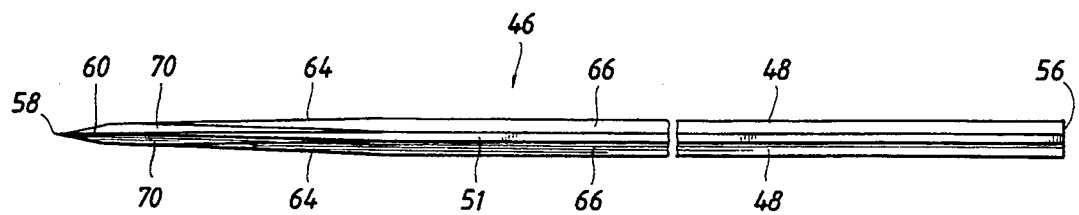
FIG. 14 is a top plan view of the blade of FIG. 13.
Figure 13:
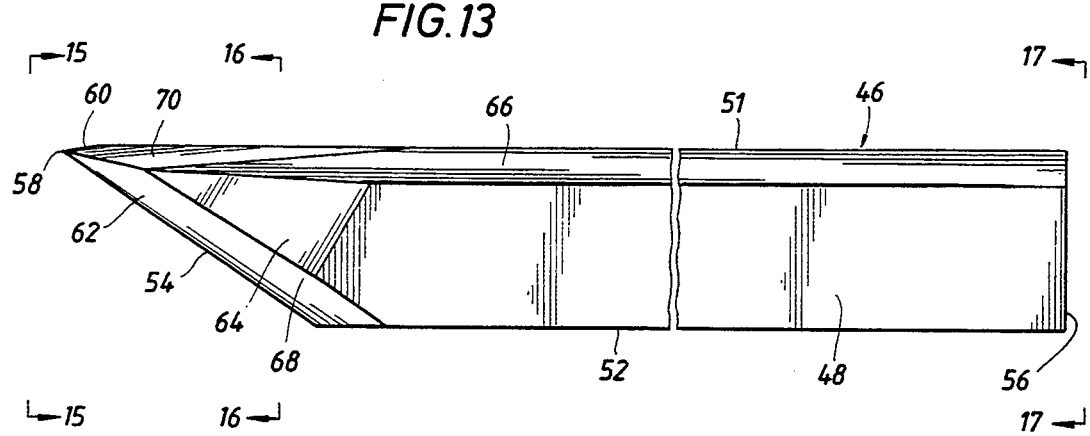
FIG. 13 is a side plan view of a second embodiment of the blade of the present invention.

FIGS. 8–12 illustrate one embodiment of the invention where a blade 36 is formed with opposing flat sides defined by reverse edge 32, a parallel edge 34, an angled forward edge 36, and a base edge 38. The forward and reverse edges 36, 32 are formed at an acute angle 40 relative to each other, preferably 35°–45°, in order to form a point 42 at their intersection. A relatively short cutting or enhancement edge 44 is formed on the reverse edge 32 adjacent to the tip 42. The enhancement edge is designed to be shorter than the depth of the incision and below the corneal layer known as Bowman's membrane, discussed above, for example, from 0.05–0.40 mm, and preferably about 0.1 millimeter ±0.0500 millimeter. The enhancement edge 44 is formed by shaping the portion of the reverse edge 32 adjacent to the tip 42 at a small angle, for example 5°–10°, as shown by arrows 46, and then forming a pair of opposing beveled surfaces 48, 50 on the flat sides 30 which are formed parallel to the angled edge 44. By forming the beveled surfaces 48, 50 in this manner, a relatively dull, flat portion 52 is formed on the reverse edge 32 adjacent to the enhancement portion 44, as best shown in FIG. 10.

Since the forward edge 36 in this embodiment is also dull, the knife does not have the capability of significantly expanding the incision. Rather, the enhancement edge 44 can only be used to correct or enhance an incision which has already been made.

Once an incision with a profile such as IA or IR, shown in FIGS. 6 and 7, has been made and a correction is deemed desirable or necessary, either at the time of the procedure or post-operatively, the blade 31 with an enhancement portion 44 can effectively be used. If the incision is one formed by the American method, as shown in FIG. 6, where the bottom of the cut is uneven or the cut is not squared off at the optical zone 24, the blade 31 is set at the desired depth of cut (typically the same depth of cut as used in making the incision unless an erroneous setting was used) and the blade 31 is inserted into the incision IA near the limbus 14, with the reverse edge 32, and consequently the enhancement portion 44, facing toward the optical zone 24.

As the surgeon retraces the incision IA, by moving in a direction opposite to the direction the knife was moved to form the initial cut, the enhancement edge 44 straightens out any unevenness at the bottom of the cut and can be used to square off the end of the cut adjacent to the optical zone 24. Since the sharp enhancement portion 44 is the only portion of the blade 31 which is able to cut tissue the surgeon can easily enhance the initial cut and make any corrections that are necessary without incision into the optical zone.

The blade 31 with an enhancement portion 44 can also be used to enhance a cut made by the Russian method (see FIG. 7) if it was not deep enough initially or squared off sufficiently at the optical zone. This can be done by simply retracing the incision IR in the same direction use to make the initial cut with the enhancement edge 44 cutting enough additional tissue to provide an incision of the proper depth or squaring off the cut at the optical zone.

In an alternative embodiment (see FIG. 13–17), an enhancement portion can be formed on a blade 46 which is universal in the sense it also has a sharpened forward edge 54. This structure allows the same blade to be used to make the initial cut when the American method shown in FIG. 6 is followed, as well as to enhance the cut by simply retracing the cut in the opposite direction. This blade could also be used to perform the enhancement procedures discussed above for the first embodiment.

Figure 15:
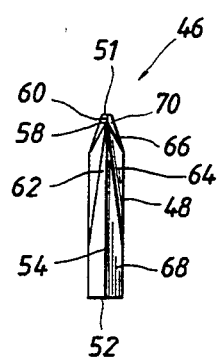
FIG. 15 is a front end view looking along the site line 15—15 of FIG. 13.
Figure 16:
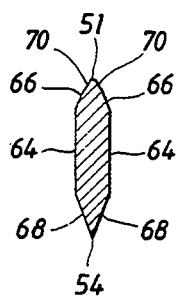
FIG. 16 is a sectional view looking along the site line 16—16 of FIG. 13.
Figure 17:
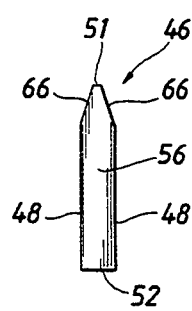
FIG. 17 is a rear end view looking along the site line 17—17 of FIG. 13.

In the second embodiment, shown in FIGS. 15–17, a blade 46 is formed with flat, opposing sides 48 that are defined by a reverse edge 51, parallel edge 52, an angled forward edge 54, and a base edge 56. Similar to the embodiment shown in FIGS. 8–12, a sharp cutting edge or enhancement portion 60 is formed on the reverse edge 51 adjacent to the tip 58. However, this blade also has a second cutting edge 62 formed on the forward edge 54.

The blade shown in FIGS. 13–17, is shaped by forming a pair of beveled surfaces 64 on the sides 48. The portion of the reverse edge 51 adjacent to the tip 58, on which the enhancement portion is formed, is formed at an angle of 10° relative to the remainder of the edge 51, as described above in conjunction with the embodiment in FIGS. 8–12.

A pair of beveled surfaces 66 are formed adjacent to the reverse edge 51 along the sides 48, at a 33° bevel. However, these beveled surfaces 66 are not necessary and can be eliminated, so the reverse edge 51 would have the same shape as the embodiment in FIGS. 10–12. The surfaces 66 do not terminate at a sharp edge, but rather at a flat, dull edge 51 as shown in particular in FIGS. 15 and 17, which cannot cut corneal tissue.

A cutting edge is formed on the forward edge 54 by forming a pair of surfaces 68, which are beveled relative to each other at 35°. The enhancement edge 60 is formed by providing a pair of beveled surfaces 70, which are beveled relative to each other at 45°, similar to the surfaces 48, 50 in FIGS. 8–12.

By providing surgical blades of the type described and illustrated with an enhancement cutting edge, RK incisions can be retraced as described if the initial cut is not considered to be close enough to the ideal profile shown in FIG. 5. This can be done without having to worry about straying off the path of the initial incision or extending an incision into the optical zone, because the enhancement portion is much shorter than the depth of the incision.

It should be understood that there can be improvements and modifications made to the embodiments of the invention described in detail above without departing from the spirit or scope of the invention, as set forth in the accompanying claims.

We claim:

1. A method for enhancing a keratorefractive surgical incision, comprising the steps of:
   (a) forming a surgical incision of a predetermined depth in the corneal stroma of a patient's eye;
   (b) enhancing the incision of step (a) by retracing the incision with a blade having a first elongated edge with distal and proximal ends, the first elongated edge including a sharp cutting portion and a dull non-cutting portion; the sharp cutting portion extending from the distal end to the dull non-cutting portion at a distance less than the depth of the incision; the dull non-cutting portion extending from the sharp edge toward the distal end.

2. The method of claim 1, wherein step (a) is performed by an elongated cutting edge on the blade opposite the first elongated edge, with a sharp cutting portion that is longer than the sharp cutting portion on the first elongated edge.

3. The method of claim 2, wherein the sharp cutting edge adjacent to the first elongated edge is shorter than the distance from the base of the incision to Bowman's membrane.

4. The surgical blade of claim 1, wherein the sharp cutting portion is about 0.05 to 0.40 mm long.

5. A method for making a keratorefractive surgical incision comprising:
   forming a surgical incision of predetermined depth in the corneal stroma of a patient's eye using a blade having a first elongated edge and a second elongated edge, the first elongated edge having distal and proximal ends and a sharp cutting portion and a dull non-cutting portion, the sharp cutting portion extending between the distal end and the dull non-cutting portion extending from the sharp edge and toward the proximal end, the sharp cutting portion having a length of about 0.05 to 0.4 mm, the second elongated edge having a sharp cutting portion longer than the sharp cutting portion of the first elongated edge, the sharp cutting portion of the second elongated edge being oriented to cut an incision in a direction which opposes the cut made with the sharp cutting portion of the first elongated edge.

* * * * *